(12) United States Patent
Salada et al.

(10) Patent No.: US 10,561,367 B1
(45) Date of Patent: Feb. 18, 2020

(54) ELECTRONIC DEVICES HAVING ADJUSTABLE FABRIC

(71) Applicant: Apple Inc., Cupertino, CA (US)

(72) Inventors: Mark A. Salada, Sunnyvale, CA (US); Michael J. Beyhs, San Francisco, CA (US)

(73) Assignee: Apple, Inc., Cupertino, CA (US)

( * ) Notice: Subject to any disclaimer, the term of this patent is extended or adjusted under 35 U.S.C. 154(b) by 42 days.

(21) Appl. No.: 15/985,538

(22) Filed: May 21, 2018

(51) Int. Cl.
*A61B 5/00* (2006.01)
*D03D 13/00* (2006.01)
*D03D 15/00* (2006.01)
*D03D 1/00* (2006.01)
*G02B 6/02* (2006.01)

(52) U.S. Cl.
CPC ............ *A61B 5/6843* (2013.01); *A61B 5/681* (2013.01); *A61B 5/742* (2013.01); *D03D 1/0088* (2013.01); *D03D 13/004* (2013.01); *D03D 15/00* (2013.01); *D03D 2700/0166* (2013.01); *D03D 2700/0174* (2013.01); *G02B 6/02057* (2013.01)

(58) Field of Classification Search
CPC combination set(s) only.
See application file for complete search history.

(56) References Cited

U.S. PATENT DOCUMENTS

| | | | | |
|---|---|---|---|---|
| 2,434,045 A * | 1/1948 | Lombardi | ................ | D04B 1/06 66/194 |
| 3,885,383 A * | 5/1975 | Tanaka | ................ | A44C 5/0023 59/79.1 |
| 5,571,175 A | 11/1996 | Vanney et al. | | |
| 5,766,131 A * | 6/1998 | Kondo | ............... | A61B 5/02416 600/310 |
| 5,906,004 A | 5/1999 | Lebby et al. | | |
| 6,977,360 B2 | 12/2005 | Weiss | | |
| 7,645,285 B2 | 1/2010 | Cosgrove et al. | | |
| 9,745,676 B2 * | 8/2017 | Hatanaka | ............... | D03D 11/00 |
| 9,830,783 B1 * | 11/2017 | Kessler | ................... | G08B 6/00 |
| 9,938,646 B2 * | 4/2018 | Hamada | ............... | D03D 47/347 |
| 10,108,151 B2 * | 10/2018 | Cardinali | ............... | G04G 21/00 |
| 10,156,029 B1 * | 12/2018 | Podhajny | ............... | G06F 3/042 |
| 10,180,721 B2 * | 1/2019 | Hoen | ...................... | G06F 3/014 |
| 10,227,721 B2 * | 3/2019 | Hatanaka | ............. | D03D 13/004 |
| 10,303,210 B2 * | 5/2019 | Mayer | ...................... | A45F 5/00 |
| 2005/0267321 A1 | 12/2005 | Shadduck | | |

(Continued)

*Primary Examiner* — Lisa Lea-Edmonds
(74) *Attorney, Agent, or Firm* — Treyz Law Group, P.C.; G. Victor Treyz; Kendall W. Abbasi

(57) ABSTRACT

Strands of material may be intertwined to form fabric for a strap or other structure in an electronic device. Conductive strands in the fabric may have middle-of-strand knots. When current is applied to a conductive strand, the knot in that strand may produce magnetic fields that cause the knot to adjust tension in the fabric. Conductive strands may intersect at nodes. Each node may have a knot formed from one or more conductive strands at the node. An electronic device or other item may have a magnetic field source that applies a fixed or time-varying magnetic field to the fabric. Each node in the fabric may include magnetic material. The magnetic material may be magnetized by applying current through the conductive strands. After magnetization, each node may interact with the magnetic field from the source of magnetic field to thereby adjust fabric tension, shape, movement, etc.

24 Claims, 14 Drawing Sheets

(56) References Cited

U.S. PATENT DOCUMENTS

| | | |
|---|---|---|
| 2006/0122544 A1 | 6/2006 | Ciluffo |
| 2006/0281382 A1* | 12/2006 | Karayianni .......... D03D 1/0088 |
| | | 442/181 |
| 2007/0144533 A1 | 6/2007 | Nelson et al. |
| 2014/0084045 A1 | 3/2014 | Yang et al. |
| 2016/0226542 A1* | 8/2016 | Tran .................... H04B 1/3888 |
| 2016/0299570 A1* | 10/2016 | Davydov ................ G06F 1/163 |
| 2017/0000415 A1* | 1/2017 | Lapetina ............. A61B 5/0006 |
| 2017/0164878 A1* | 6/2017 | Connor .................. G09B 23/28 |
| 2017/0247820 A1* | 8/2017 | Podhajny ............. D03D 1/0088 |
| 2017/0370030 A1* | 12/2017 | Podhajny ............. D03D 1/0088 |
| 2018/0363173 A1* | 12/2018 | Keating ............. D03D 15/0083 |
| 2019/0013274 A1* | 1/2019 | Sunshine ................ H01L 33/62 |
| 2019/0013275 A1* | 1/2019 | Sunshine ............ H01L 23/5386 |
| 2019/0136423 A1* | 5/2019 | Podhajny ............... D03D 15/00 |

* cited by examiner

US 10,561,367 B1

ELECTRONIC DEVICES HAVING ADJUSTABLE FABRIC

FIELD

This relates generally to electronic devices and, more particularly, to electronic devices that include fabric.

BACKGROUND

It may be desirable to form electronic device structures from fabric. For example, a wristwatch may have a fabric strap. If care is not taken, fabric structures may not perform as desired. For example, a fabric strap may be uncomfortably tight or may be too loose. In some situations, tension variations in fabric straps for wristwatches can hinder accurate wristwatch sensor measurements.

SUMMARY

Strands of material may be intertwined to form fabric. The fabric may be configured to form a strap or other structure for an electronic device. The electronic device may include input-output devices such as sensors, buttons, displays, and other components.

Conductive strands in the fabric may have knots such as middle-of-strand knots. When current is applied to a conductive strand, the knot in that strand may produce magnetic fields that cause the knot to adjust tension in the fabric. Fabric tension adjustments may cause motion in the fabric and changes in the shape of the fabric.

Conductive strands may intersect at nodes. Each node may have a knot formed from loops of one or more conductive strands. An electronic device or other item may have a magnetic field source that applies a fixed or time-varying magnetic field to the fabric. The magnetic fields produced by the knots may interact with the magnetic field produced by the magnetic field source.

Nodes in the fabric may include magnetic material. The magnetic material may be magnetized by applying current through the conductive strands. After magnetization, the magnetic material may interact with magnetic fields produced by other magnetized magnetic material at the nodes and/or magnetic field from the source of magnetic field. These interactions may serve to adjust fabric tension, shape, movement, etc.

Nodes may include gating circuits. The gating circuits may have gating devices such as transistors, photosensitive circuits, or other circuitry that allows the gating circuits to control current flow through knots at the nodes based on control input. During operation of an electronic device, control circuitry in the electronic device may apply currents to mid-strand knots and other structures formed in the fabric to adjust the shape, tension, and/or movement of the fabric.

To provide the control circuitry with feedback, sensing circuitry can be incorporated into the fabric. The sensing circuitry may be used to measure fabric bending and other activities and may therefore be used in providing feedback to the control circuitry.

DETAILED DESCRIPTION

Figure 1:
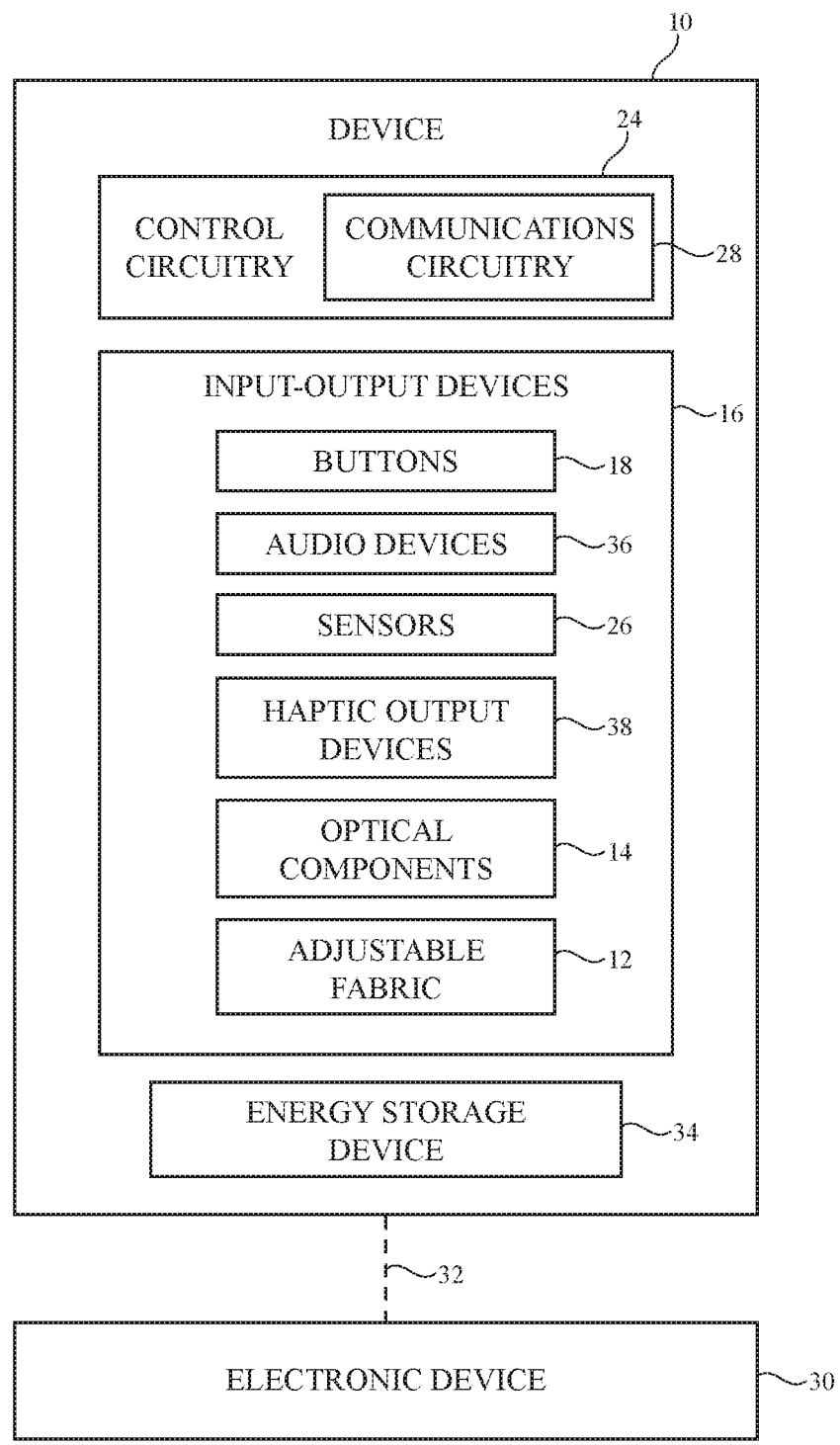
FIG. 1 is a schematic diagram of an illustrative electronic device in accordance with an embodiment.

Items such as electronic device 10 of FIG. 1 may be used to gather input from a user and the surrounding environment and may be used to supply a user with output. As an example, device 10 may be a wristwatch device that monitor's a user's pulse, a user's blood pressure, and other health characteristics, that makes other sensor measurements, and that provides the user with visual output, audible output, and/or haptic output. Device 10 may have a strap or other structures that allow device 10 to be worn on a user's body. For example, device 10 may have a band-shaped strap that allows device 10 to be worn on a user's wrist. The strap and/or other structures in device 10 can include fabric. In some arrangements, the fabric can be adjusted. For example, the fabric may include nodes that can be adjusted to selectively increase or decrease tension in various portions of a layer of fabric. This allows device 10 to buckle a fabric region to provide a user with haptic output and/or to adjust the size and/or shape of device 10. For example, device 10 may have a wrist strap formed from adjustable fabric that can be tightened when it is desired to gather sensor measurements on a user's wrist and that can be loosened when it is desired to wear the wrist strap normally.

Electronic device 10 may be a stand-alone electronic device and/or may operate as an accessory that is used with ancillary electronic equipment. Device 10 may, as an example, be an electronic device such as a laptop computer, a computer monitor containing an embedded computer, a tablet computer, a cellular telephone, a media player, or other handheld or portable electronic device, a smaller device such as a wrist-watch device, a pendant device, a headphone or earpiece device, a device embedded in eyeglasses or other equipment worn on a user's head, or other wearable or miniature device, a television, a computer display that does not contain an embedded computer, a gaming device, a navigation device, a remote control, an embedded system such as a system in which device 10 is mounted in a kiosk, in an automobile, airplane, or other vehicle, other electronic equipment that includes adjustable fabric, or equipment that implements the functionality of two or more of these devices. If desired, device 10, which may sometimes be referred to as a fabric-based item or system, may be a removable external case for electronic equipment, may be a strap, may be a wrist band or head band, may be a removable cover for a device, may be a case or bag that has straps or that has other structures to receive and carry electronic equipment and other items, may be a necklace or arm band, may be a wallet, sleeve, pocket, or other structure into which electronic equipment or other items may be inserted, may be part of a chair, sofa, or other seating (e.g., cushions or other seating structures), may be part of an item of clothing or other wearable item (e.g., a hat, belt, wrist band, headband, sock, glove, shirt, pants, etc.), or may be any other suitable item.

Device 10 may have structures such as outer layers (e.g., the outermost layer in a housing), inner layers (e.g., layers that are overlapped by the outermost layer in device 10), and internal support structures that are formed from glass, metal, polymer, ceramic, wood, fabric, natural materials such as leather, and/or other materials. These layers of material may include rigid portions and flexible portions. In some configurations, the outermost layers of device 10 that form external surfaces for device 10 may be formed from flexible material.

Fabric in device 10 may be woven fabric, knit fabric, braided fabric, or fabric formed using strands of material formed using other strand intertwining techniques. By selecting materials such as fabric and/or other materials for the housing of device 10, device 10 may configured to be soft (e.g., device 10 may have a fabric surface that yields to a light touch), may be configured to have a rigid feel (e.g., the surface of device 10 may be formed from a stiff fabric or hard polymer or other material), may be coarse, may be smooth, may have ribs or other patterned textures, and/or may have other configurations.

Device 10 may have control circuitry 24. Control circuitry 24 may be formed from one or more integrated circuits such as microprocessors, microcontrollers, application-specific integrated circuits, digital signal processors, and/or other circuits and may be used to control the operation of electronic device 10 by controlling electrically controllable (electrically adjustable) components in device 10. Control circuitry 24 may use communications circuitry 28 to support communications with one or more devices such as electronic device 30 (e.g., a wristwatch main unit, a cellular telephone or other portable device, wireless earbuds or other audio accessories, etc.). Device 30 may be attached to and/or incorporated into electronic device 10 (e.g., when device 10 is a strap for a wristwatch and device 30 is the main unit of the wristwatch) or electronic device 10 and electronic device 30 may be separate items that are configured to operate with each other (e.g., when one device is a case and the other is a device that fits within the case, etc.). Circuitry 28 may include antennas and other structures for supporting wireless communications with device 30 over communications link 32. Link 32 may be a wired communications link or may be a wireless communications link.

Device 30 may be an electronic device such as a cellular telephone, computer, or other portable electronic device and device 10 may form a cover, case, bag, or other structure that receives the electronic device in a pocket, an interior cavity, or other portion of device 10. In other situations, device 30 may be a wristwatch unit or other electronic device and device 10 may be a strap or other fabric-based item that is attached to device 30 (e.g., device 10 and device 30 may be used together to form a device such as a wristwatch with a strap). In still other situations, device 10 may be an electronic device (e.g., a wearable device such as a wrist device, arm band, hat, glove, clothing, etc.) and additional devices such as device 30 may include accessories or other devices that interact with device 10 such as wireless speakers, wireless ear buds, etc. Signal paths formed from conductive yarns and monofilaments (e.g., insulated and bare wires), metal traces on printed circuits, and/or other conductive paths may be used to route signals in device 10 and/or device(s) 30.

Device 10 may include input-output devices 16. Input-output devices 16 may be used to gather input from a user and to make measurements on the operating environment for device 10. Input-output devices 16 may also be used in providing output. The output that is provided may be visual output, audio output, haptic output, wirelessly transmitted output, and/or other output. Output may include alerts (e.g., notifications of incoming messages, alarm timer alerts, calendar alerts, etc.), status information (e.g., battery status), time information, icons, text, graphics, video, audible alerts, haptic output (e.g., vibrating alerts, etc.), information on sensor measurements, and/or other output.

Input-output devices 16 may include buttons 18 (push buttons, rotary buttons, slider buttons, etc.). Input-output devices 16 may also include audio devices 36 (e.g., microphones and/or speakers). Sensors 26 in input-output devices 16 may include touch sensors (e.g., an optical touch sensor, an acoustic touch sensor, a capacitive touch sensor, or other suitable touch sensor) and/or force sensors (e.g., force sensors based on piezoelectric sensors, strain gauges, resistive force sensors, capacitive force sensors and/or other force sensors). Touch sensors and force sensors may, if desired, be implemented using conductive strands in fabric (e.g., conductive strands forming capacitive sensor electrodes in a capacitive touch and/or force sensor). Sensors 26 may also include gas pressure sensors, particulate sensors, ambient light sensors, optical proximity sensors, optical sensors such as cameras for gathering three-dimensional gesture input, infrared cameras and light sources (e.g., for iris scanning), temperature sensors, other optical sensors, gaze tracking sensors, sensors for measuring position and/or orientation such as accelerometers, gyroscopes, magnetic sensors (compasses) and/or inertial measurement units that contain multiple orientation sensors and/or position sensors, blood pressure sensors, heartbeat sensors, sensors for measuring electrocardiograms, electromyography sensors, blood oxygen sensors, other health monitoring sensors, and/or other sensors.

Haptic output devices 38 may be based on piezoelectric actuators, electromagnetic actuators, electroactive polymers, motors, vibrators, and/or other devices for providing haptic output.

Optical components 14 may include displays for displaying images (e.g., images with text, photographs, graphics, movies, etc.). Displays may be organic light-emitting diode displays, displays having pixel arrays formed from crystalline semiconductor light-emitting diodes, liquid crystal displays, electrophoretic displays, and other displays. Components 14 may also include light-emitting diodes and/or other light-emitting devices that have lower resolution than displays. For example, light-emitting diodes may directly supply illumination to an icon-shaped pattern of openings in a layer of material in device 10 or may supply illumination to a light guide layer that provides the illumination to an icon-shaped pattern of openings in a layer of material in device 10.

To power device 10, device 10 may include a battery, supercapacitor, or other energy storage device 34.

Adjustable fabric 12 may be used to provide a user with haptic output (e.g., by buckling a selected portion of fabric 12 to press against a user's skin), may be used to tighten and/or loosen a strap, may be used to change the shape of a portion of device 10, and/or may otherwise be adjusted during operation of device 10. Fabric 12 may be adjusted by supply electrical signals to conductive strands of material in fabric 12. The conductive strands may include knots such as mid-strand knots (sometimes referred to as middle-of-strand knots, middle-of-strand loops, etc.). When a current is applied to the knots, magnetic fields are created that give rise to torque and associated movement and change in shape of portions of the knots and associated fabric. For example, portions of fabric 12 may experience changes in tension and may tighten or loosen and/or may buckle or otherwise change shape.

Figure 2:
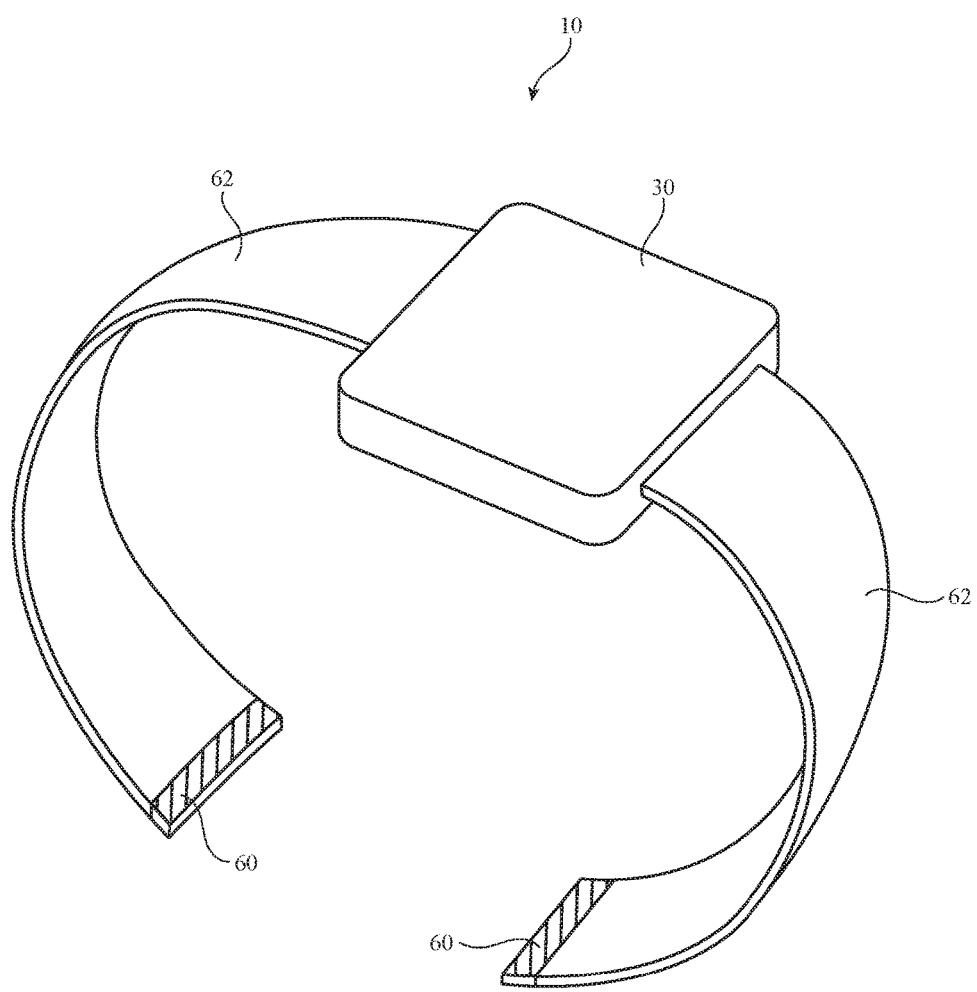
FIG. 2 is a perspective view of an illustrative electronic device with adjustable fabric being used to form a strap in accordance with an embodiment.

FIG. 2 is a perspective view of an illustrative wristwatch device of the type that may include an adjustable strap. Wristwatch device 10 may have a strap such as strap 62 that is formed from adjustable fabric 12. In the example of FIG. 2, the strap is coupled to watch device 30 (e.g., a touch-enabled wristwatch unit having a touch screen, one or more buttons, wireless circuitry for transmitting and receiving wireless information, and/or other components). As shown in FIG. 2, the wristwatch may include a clasp such as clasp 60. Clasp 60 may include magnets, interlocking mechanical features, and/or other clasp structures for securing the ends of the strap together. If desired, clasp 60 may be omitted (e.g., when the strap is elastic). During operation, sensors 26 may gather input through inner and outer surfaces of strap 62 while input-output devices 16 supply visible output, haptic output, and other output through surfaces 62 of device 10. Device 30, which may include circuitry and components for device 10 (see, e.g., the circuitry and components of FIG. 1), may also use sensors such sensors 26 to gather input while using input-output devices such as devices 16 of FIG. 1 to provide output.

Figure 3:
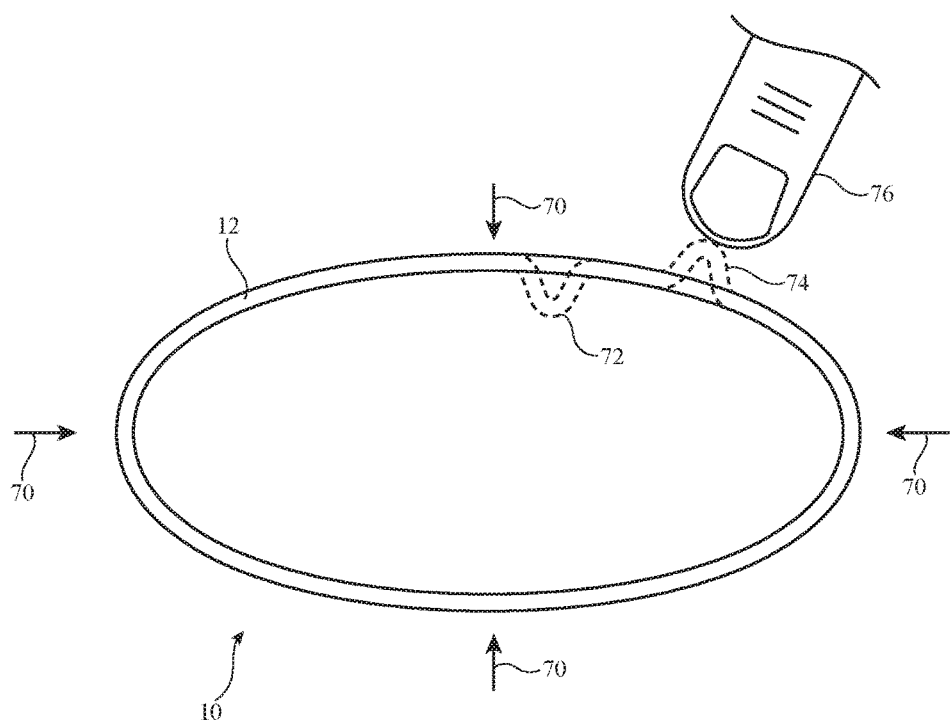
FIG. 3 is a side view of an illustrative device formed from adjustable fabric in accordance with an embodiment.

FIG. 3 is a side view of an illustrative device 10 in a configuration in which device 10 is a strap configured to be worn on a user's wrist or other body part. The strap may be formed from adjustable fabric 12. An optional device such as device 10 of FIG. 2 may, if desired, be coupled to the strap. Control circuitry 24 may be incorporated into device 10 (e.g., in fabric 12) to control the shape of adjustable fabric 12 during operation. For example, control circuitry 24 can apply current to conductive strands of material in fabric 12 to cause fabric 12 to contract inwardly (e.g., to radially contract) in directions 70 (e.g., to grasp onto a user's body so that a blood pressure sensor in sensors 26 can make an accurate measurement). Fabric 12 can also be adjusted by control circuitry 24 so that a portion of fabric 12 forms an inwardly directed protrusion such as protrusion 72 or an outwardly directed protrusion such as protrusion 74. Protrusion 72 may provide haptic output to a user's wrist or other body part on which device 10 is being worn. Protrusion 74 may provide haptic output to a user's finger such as finger 76. If desired, a touch sensor or other input device and a visual output device (e.g., a display, light-emitting diode(s), etc.) can provide visual output in a portion of device 10 that overlaps a haptic output region (e.g., to implement a button that is illuminated with an icon or other label and that provides haptic feedback when selected).

Figure 4:
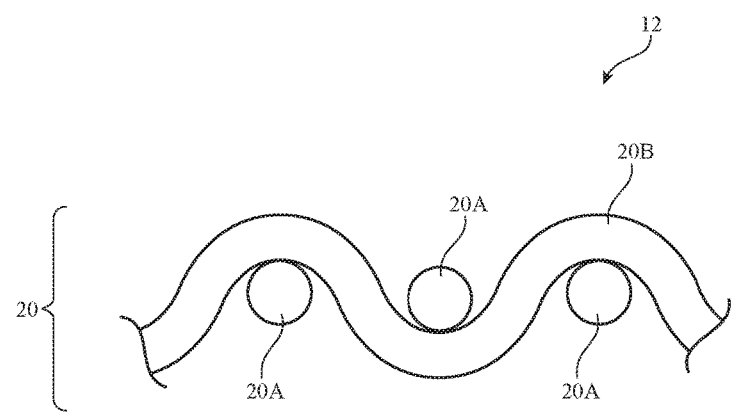
FIG. 4 is a side view of illustrative fabric in accordance with an embodiment.

Fabric 12 may be woven fabric, knitted fabric, fabric formed by braiding, and/or other suitable fabric. With one suitable arrangement, which may sometimes be described herein as an example, fabric 12 may be woven fabric such as fabric 12 of FIG. 4. As shown in FIG. 4, fabric 12 may include intertwined strands of material such as strands 20 (e.g., warp strands 20A and weft strands 20B). In the illustrative configuration of FIG. 4, fabric 12 has a single layer of woven strands 20. Multi-layer fabric constructions may be used for fabric 12 if desired.

The strands of material in fabric 12 may be single-filament strands (sometimes referred to as fibers or monofilaments), may be yarns or other strands that have been formed by intertwining multiple filaments (multiple monofilaments) of material together, or may be other types of strands. Strands 20 in fabric 12 may include insulating strands and conductive strands. Conductive strands may include bare wires and/or insulated wires. Conductive strands may also be formed from insulating strands covered with metal coatings and strands formed from three or more layers (cores, intermediate layers, and one or more outer layers each of which may be insulating and/or conductive). Strands 20 may be from polymer, metal, glass, graphite, ceramic, natural materials as cotton or bamboo, or other organic and/or inorganic materials and combinations of these materials. Conductive yarns may be formed from a bundle of bare metal wires, metal wire intertwined with insulating monofilaments, and/or other conductive strands. Solder, welds, crimped connections, conductive adhesive connections, and/or other connections may be used to electrically and/or mechanically attach circuitry to strands in fabric 12.

Figure 5:
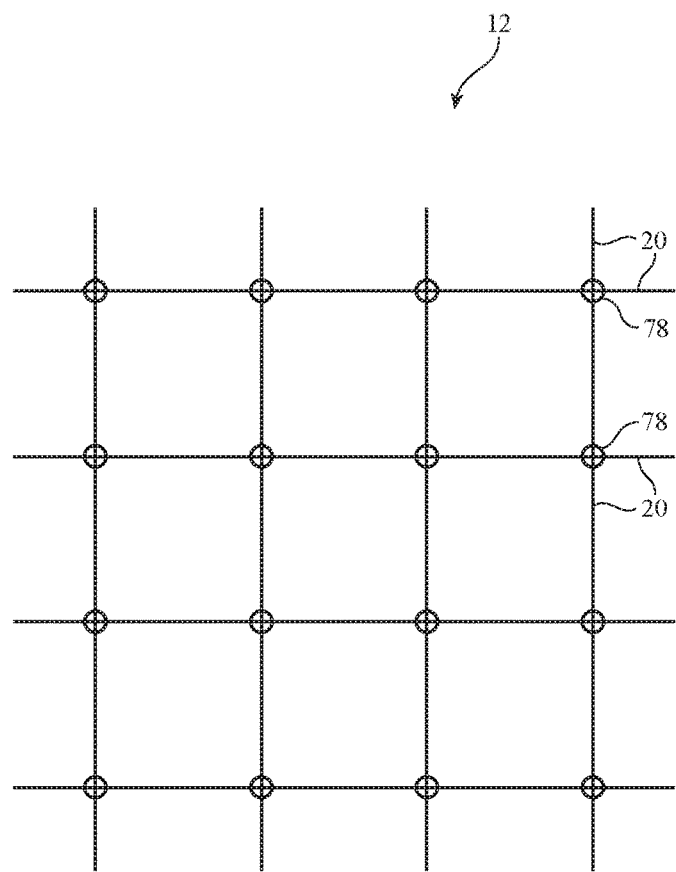
FIG. 5 is a top view of illustrative adjustable fabric in accordance with an embodiment.

As shown in the illustrative configuration of FIG. 5, fabric 12 may have strands 20 that intersect at nodes 78. Nodes 78 may include knots (e.g., loops of conductive strands that are intertwined in a secure fashion to prevent unraveling) and may include other structures that can be adjusted by selective application of electrical signals (e.g., currents) by control circuitry 24. Each nodes 78 may, as an example, include one or more knots formed in the middle of a strand 20 (sometimes referred to as mid-strand knots, mid-strand loops, or middle-of-strand loop knots). If desired, nodes 78 may be formed by knots (e.g., mid-strand knots) associated with multiple strands (e.g., two or more intersecting strands may be used to form mid-strand knots at a given node). By applying signals to various strands 20, the knots can be used to generate magnetic fields that, in turn, create forces (e.g., torque that tends to twist the knots) and thereby adjust tension in the strands. By adjusting fabric tension at various locations within fabric 12, fabric 12 can be caused to contract globally (e.g., to tighten a band about a user's wrist) may be caused to relax globally (e.g., to loosen a band), may be caused to fold in an accordion pattern (e.g., to tighten a band by bucking upwards and downwards in alternating rows or columns of nodes), may be caused to protrude or create a recess in one or more locations on fabric 12, may be caused to vibrate, and/or may otherwise be directed to move and change shape.

Figure 6:
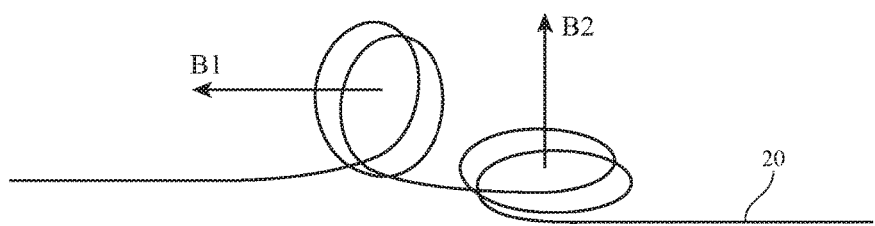
FIG. 6 is a perspective view of a conductive strand having loops that create interacting magnetic fields in accordance with an embodiment.

FIG. 6 is a perspective view of an illustrative strand with interacting loops showing how magnetic fields can be adjusted to adjust tension in the strand. When a current is applied through strand 20 of FIG. 6 by control circuitry 24, a first set of loops create magnetic field B1 and a second set of loops create magnetic field B2. Fields B1 and B2 will tend to orient in the same direction, which adjusts the tension in strand 20 along its length. To ensure that the loops of strand 20 remain in place in fabric 12, these loops may form part of a mid-strand knot (e.g., a knot at a node 78).

Figure 7:
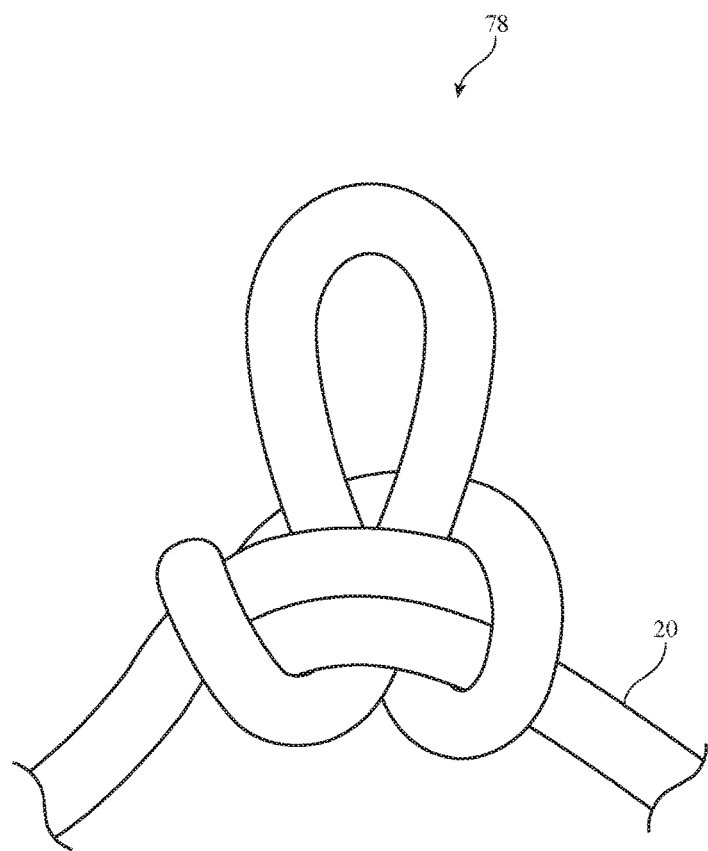
FIG. 7 is a perspective view of an illustrative mid-strand knot in accordance with an embodiment.

An illustrative strand with a node 78 that has been formed from a mid-strand knot (mid-strand loop) is shown in FIG. 7. The illustrative mid-strand knot formed in FIG. 7 is an alpine butterfly loop. Other knot types may be used, if desired. For example, node 78 may be formed from a knot in strand 20 such as a figure eight directional knot, a bowline on a bight knot, a double alpine butterfly loop knot, a dropper loop knot, a figure eight double loop knot, a figure eight follow through knot, a handcuff knot, an a Spanish bowline knot (as examples).

Figure 8:
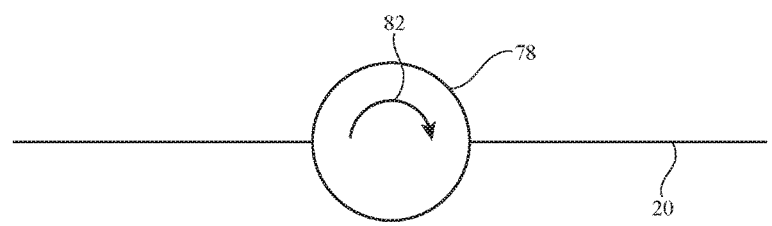
FIGS. 8 and 9 are schematic diagrams of illustrative knots for use in adjustable fabric in accordance with an embodiment.

As shown schematically in FIG. 8, a given strand 20 in fabric 12 may have a knot forming node 78 that creates torque and thereby rotates in a first direction such as illustrative direction 82 when current is driven through the strand.

Figure 9:
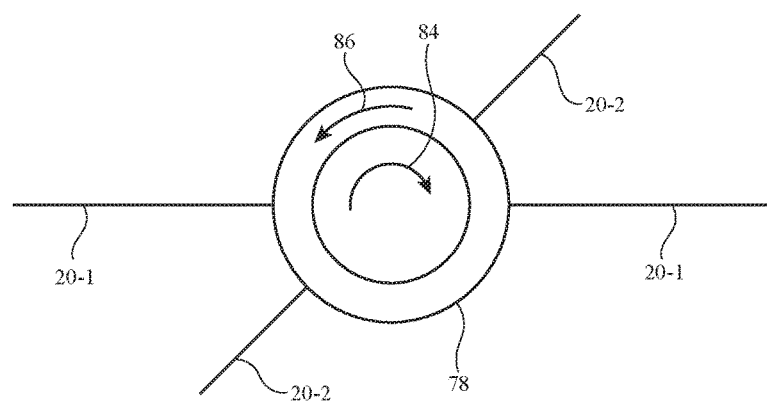

As shown in FIG. 9, two strands 20 (e.g., strands 20-1 and 20-2) that intersect at a node 78 may have respective mid-strand knot portions that are configured to create, respectively, torque and rotation in directions 84 and 86. Depending on the relative currents driven through strands 20-1 and 20-2, the torques produced by the first and second knot portions may tend to add to each other or may tend to cancel each other.

Figure 10:
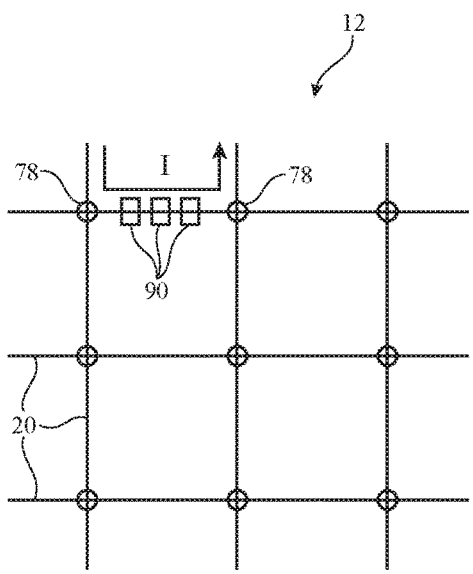
FIGS. 10 and 11 are top views of illustrative adjustable fabric in accordance with an embodiment.

If desired, electrical components (e.g., input-output devices 16) can be incorporated into mid-strand knots (e.g., at nodes 78) and/or may otherwise be coupled to strands 20 (e.g., electrical components may be coupled to conductive strands using solder or other conductive connections at locations in fabric 12 such as at nodes 78). FIG. 10 shows how mid-strand knots and/or electrical components (e.g., input-output devices 16) may be located at strand intersection points (e.g., nodes 78) and/or at strand locations between strand intersections (see, e.g., illustrative nodes 90).

Figure 11:
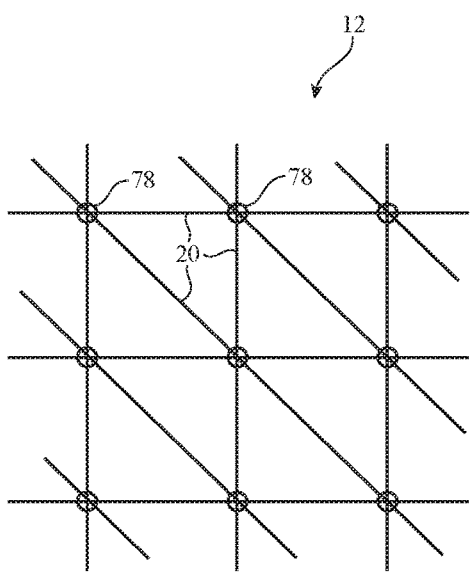

During operation, control circuitry 24 can control current flow through horizontal strands, vertical strands, and/or other conductive strands in fabric 12. Solder and/or other electrical connections (shorts) can be created between overlapping conductive strands 20. In this way, current paths such as the illustrative path of current I in FIG. 10 may be created to control the current through mid-strand knots and/or electrical components at locations such as nodes 78 and/or nodes 90. FIG. 11 shows how fabric 12 may include strands 20 that run diagonally through fabric 12 (e.g., fabric 12 may include diagonal strands 20 in addition to orthogonal warp and weft strands). The strands of FIGS. 10 and 11 may be provided with control signals in any suitable patterns. For example, the strands in even rows of fabric 12 may receive positive current while the strands in odd rows of fabric 12 may receive negative current, while intersecting strands in even and/or odd columns allow current to flow between rows (as an example).

Magnetic materials (e.g., iron or other materials) can be incorporated into fabric 12. For example, a magnetizable material such as iron may be located at each node 78. When current is applied through a loop that runs around an iron member, the loop may serve as an electromagnet and may repel and/or attract other magnetic material, permanent magnets, and/or electromagnets. In some arrangements, an iron bar or other member formed form magnetic material can be magnetized by application of current through a strand 20 that loops around that member. The resulting magnet formed from the iron bar or other magnetic material may then magnetically interact with structures formed from magnetic materials such as electromagnets, permanent magnets, etc. In this way, current can be applied to a node 78 to create a magnet (e.g., by magnetizing an iron bar) and this magnet will persist after the current is removed. This allows the torque produced by the magnet (and its interactions with nearby objects) to persist, even though no current is being actively driven through the strand. This arrangement mat thereby help to reduce power consumption.

Figure 12:
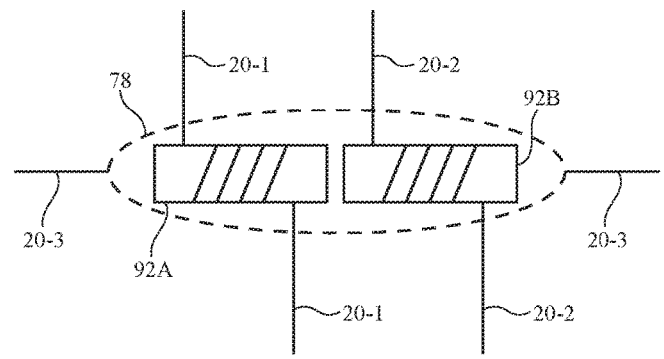
FIG. 12 is a diagram of an illustrative adjustable fabric node based on a pair of magnetic structures looped with conductive strands in accordance with an embodiment.

FIG. 12 shows an illustrative node 78 with first and second magnetic members 92A and 92B, respectively. Members 92A and 92B may be wound with loops of first strand 20-1 and second strand 20-2, respectively. Adhesive, a knot (e.g., a mid-strand knot formed by strand 20-1 and/or 20-3), a clip, a hinged structure, or other coupling mechanisms may be used in securing members 92A and 92 within node 78. These securing mechanisms may allow members 92A and 92B to reorient with respect to each other and thereby adjust tension in fabric 12.

Figure 13:
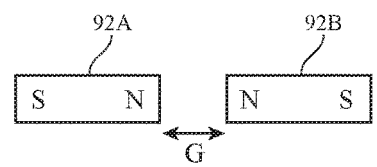
FIGS. 13, 14, and 15 are diagrams of illustrative magnetic elements in different interaction configurations in accordance with an embodiment.
Figure 14:
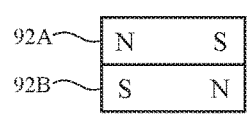
Figure 15:
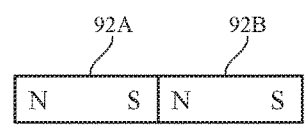

If desired, additional strands such as illustrative strand 20-3 may be coupled to members 92A and 92B. Additional strands such as strand 20-3 may be insulating and/or may be conductive. Optional strand 20-3 may, as an example, have a first portion that is coupled to a first side of node 78 and a second portion that is coupled to a second side of node 78. By applying current through strands 20-1 and 20-2, members 92A and 92B (e.g., iron bars or other magnetizable magnetic core members) can be provided with magnetic poles that repel one another (see, e.g., FIG. 13 in which a gap G is created separating members 92A and 92B), that attract each other so that members 92A and 92B lie side by side (FIG. 14), and/or that attract each other so that members 92A and 92B lie end to end (FIG. 15). Other illustrative configurations for node 78 can be created if desired. Each different configuration for members 92A and 92B may create different tensions on strands 20-1, 20-2, and optional additional strand(s) coupled to node 78 such as strand 20-3.

Figure 16:
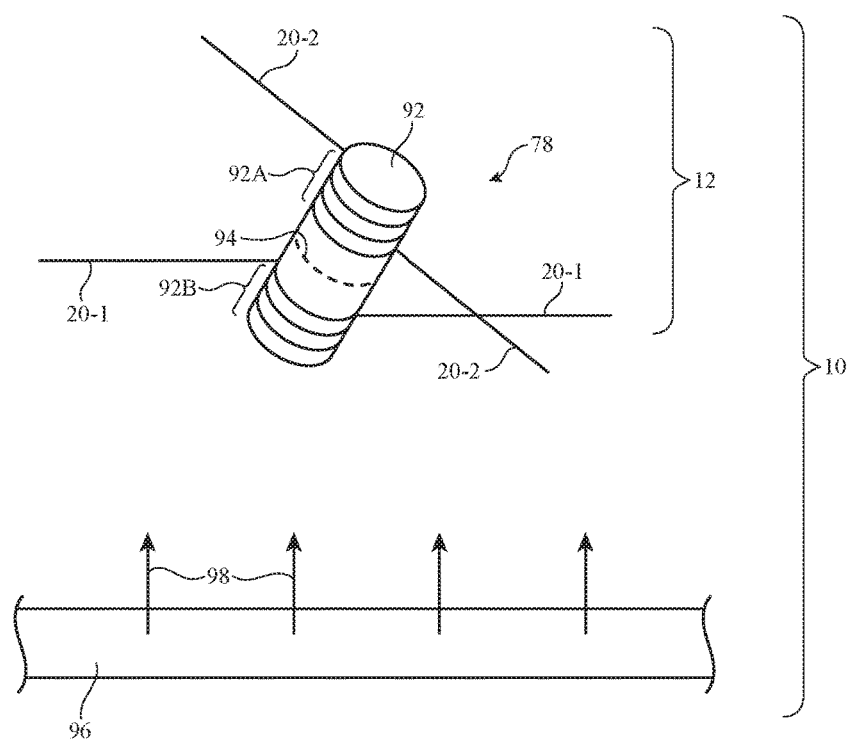
FIG. 16 is a diagram of an illustrative adjustable magnetic element that is interacting with a magnetic field from a magnet in accordance with an embodiment.

As shown in FIG. 16, device 10 may have a source of magnetic field such as magnetic field source 96. Magnetic field source 96 may be formed from a magnetized magnetic layer (e.g., a sheet magnet), a permanent magnet, an electromagnet, bar magnets, and/or other sources of fixed and/or time-varying magnetic field to be applied to fabric 12 (e.g., globally and/or in selected locations of fabric 12). Magnetic field source 96 may provide a magnetic field such as magnetic field 98 that interacts with electromagnets and/or permanent magnets formed at each node 78. As an example, node 78 may include a magnetic structure (e.g., a member such as member 92 formed from magnetic material) and this magnetic structure may be provided with a magnetic field by applying signals to the strand(s) of that node that interacts with magnetic field 98.

Strands 20 such as strands 20-1 and 20-2 may be looped about each other and/or about magnetic structure 92. For example, strand 20-1 may form one or more loops on portion 92B of member 92 and strand 20-2 may form one or more loops on portion 92A of member 92. Member 92 may be a single piece of material (e.g., an iron member such as an iron bead, etc.) and/or may be formed from multiple pieces of material that are joined together. For example, portions 92A and 92B may be coupled together at optional coupling 94 (e.g., using a hinge, a sliding coupling structure, or other coupling mechanism). When current is applied to one or more strands 20 in fabric 12 such as strands 20-1 and 20-2 of FIG. 16, magnetic field will be created that will cause member 92 to move relative to magnetic field 98. The signals applied to strands 20 by control circuitry 24 can be controlled in this way to adjust the resulting tension of strands 20. Tension can be controlled in fabric 12 along lines of nodes 78 or other regions of fabric 12, on selected individual nodes 78, or on all of fabric 12 globally.

In some configurations, some or all of member 92 may be magnetized by application of current to stands 30. In this type of arrangement, power can be conserved, because each node 78 can retain a desired amount of magnetization after the magnetizing current has been removed. In this state, a permanent magnet will be formed at each node 78 that experiences force due to its interaction with magnetic field 98. When it is desired to remove a permanent magnet that has been formed in a given member 92, the polarity of the applied current can be reversed.

Figure 17:
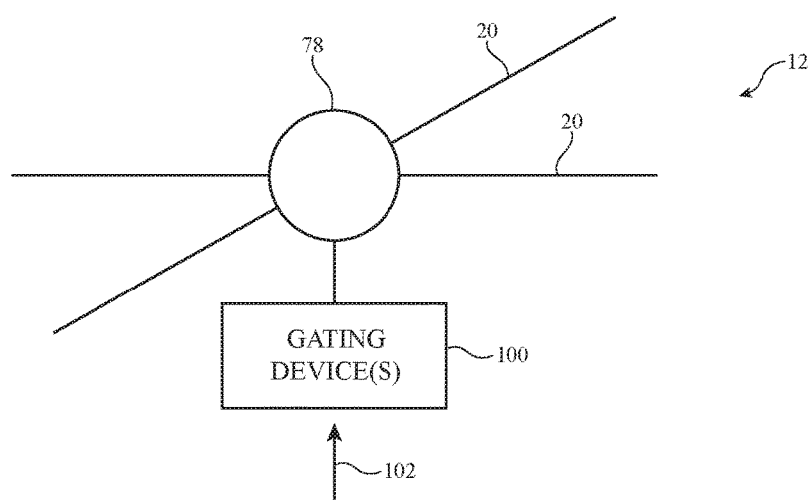
FIG. 17 is a diagram of an illustrative adjustable fabric node with a gating device in accordance with an embodiment.

FIG. 17 shows how gating device(s) (sometimes referred to as gating circuitry) may be incorporated into fabric 12 and/or used with fabric 12 to adjust the application of signals to nodes 78. Gating devices 100 (e.g., photodiodes, phototransistors, transistors, transistor-based circuits, circuits with force transducers, optical transducers, and/or other circuitry) can be configured to adjust signals applied to each node 78 based on input 102 (e.g., based on optical signals, based on electrical control signals from control circuitry 24, based on forces applied to force-transducing gating devices, etc.). Consider, as an example, a scenario in an array of gating devices 100 is associated with an array of corresponding nodes 78. Patterned input (optical, electrical, force, etc.) can be applied to gating devices 100 across fabric 12. In response, each gating device 100 may supply a corresponding control signal to a respective node 78. The knots and/or other structures at each node will cause strands 20 near each node to be tensioned by a corresponding amount, thereby causing fabric 12 to change tension and/or shape in a desired pattern.

Figure 18:
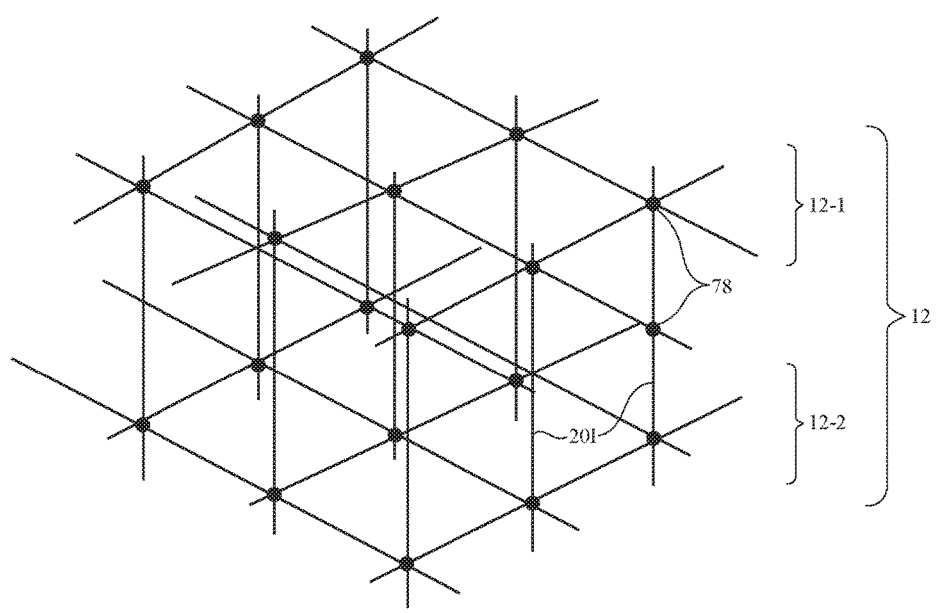
FIG. 18 is a perspective view of illustrative three-dimensional fabric in accordance with an embodiment.

Fabric 12 may, if desired, include one or more fabric layers (e.g., fabric 12 may be a three-dimensional fabric having at least two layers, at least three layers, at least four layers, and/or other number of layers). An illustrative three-dimensional fabric in which strands 20I are configured to extend between respective fabric layers 12-1 and 12-2 is shown in FIG. 18. Strands 20I may carry electrical signals and/or may include insulating strands. Each node 78 may include a mid-strand knot and/or other structures that allow node 78 to apply controllable amounts of tension to associated strands 20.

As fabric 12 is tensioned in various locations and changes shape, it may be desirable to provide control circuitry 24 with feedback indicative of the amount of induced tension and/or shape change. If desired, sensors may be incorporated into fabric 12 to provide control circuitry 24 with information on the tension and shape of fabric 12.

Figure 19:
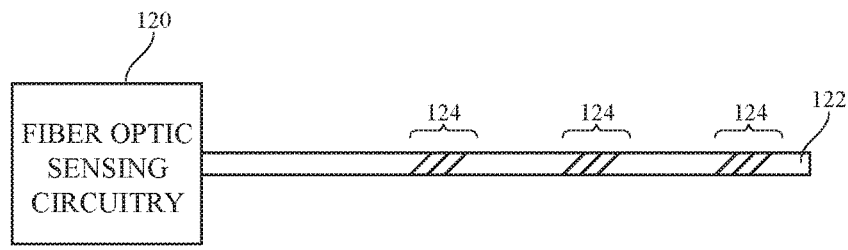
FIG. 19 is a diagram of an illustrative fiber-based sensor for detecting bending adjustable fabric in accordance with an embodiment.

With one illustrative configuration, fiber-based sensing systems may be used to monitor fabric 12. As shown in FIG. 19, an optical fiber such as optical fiber 122 may be provided with gratings 124. Fiber 122 may be incorporated into fabric 12 with other strands 20. Fiber-optic sensing circuitry 120 may include a laser or other light source that emits light into fiber 122 (sometimes referred to as an optically transparent strand or light guiding strand). Fiber-optic sensing circuitry 120 may also include a light detector that receives emitted light that has been received at circuitry 120 after being reflected backwards towards circuitry 120 from gratings 124. By analyzing the reflected light (e.g., for frequency, intensity, etc.), fiber optic sensing circuitry 120 can measure bending in fiber 122. one or more optically transparent strands 20 such as illustrative fiber 122 can be incorporated into fabric 12, so that fiber optic sensing circuitry 120 can measure the shape of fabric 12 in two dimensions.

Figure 21:
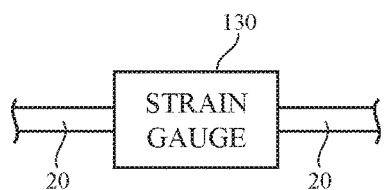
FIG. 21 is a diagram of an illustrative strain gauge in accordance with an embodiment.

Sensing circuitry for gathering feedback on the state of fabric 12 can also be based on force sensors such as force-sensitive resistors. An illustrative force sensitive resistor circuit for measuring the state of fabric 12 is shown is shown in FIG. 21. As shown in FIG. 21, force sensing resistor 126 may be incorporated into fabric 12 (e.g., by coupling one or more strands 20 to resistor 126, by incorporating resistors 126 into knots and/or other structures at nodes 78, by including resistors such as resistor 126 in nodes 90, etc.). As tension is created in portions of fabric 12, the resistance of resistor 126 changes and this change in resistance is measured by resistance measurement circuitry 128.

FIG. 21 shows how device 10 may include a force sensing arrangement such as a strain gauge or other force sensor that measures tension in fabric 12. Strain gauge 130 may be directly or indirectly coupled to strands 20 in fabric 12. As fabric 12 is tensioned and/or changes shape, changes in force may be produced at strain gauge 130. Control circuitry 24 can use these strain gauge measurements, for example, to determine how tightly a fabric strap has been tensioned about a user's wrist.

If desired, control circuitry 24 can apply alternating-current signals (e.g., control signals and/or sensing signals) to conductive strands in fabric 12 while measuring the impedance of these conductive strands. The impedance of the conductive strands may be affected by tension (e.g., due to changes in knot shape, fabric buckling, and/or other changes in the conductive strands). By monitoring the impedance of the conductive strands in fabric 12, control circuitry 24 can gather information on the state of fabric 12 (e.g., feedback associated with bending, tension, movement of strands, etc.).

Figure 20:
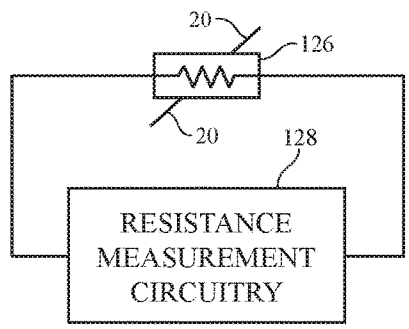
FIG. 20 is a diagram of an illustrative force-sensing resistor in accordance with an embodiment.

Feedback on force, bending, movement, and/or other status information on fabric 12 and other portions of device 10 may, in general, be gathered using any suitable sensors 26. These sensors may be located in fabric 12, may be coupled directly to fabric 12 with adhesive or other coupling mechanisms, and/or may be coupled to fabric 12 indirectly. The use of optical measurement circuits such as the optical fiber force and bending sensor arrangement of FIG. 19, the force-sensitive resistor sensing arrangement of FIG. 20, and the strain gauge sensing system of FIG. 21 are illustrative. Feedback measurements can be used to form a closed-loop control system in device 10 and/or to gather user input or other input (e.g., input on movement of body parts coupled to fabric 12, input on movement of a button region in fabric 12 that is being pressed by a finger or other external object, etc.).

During operation, control circuitry 24 may apply signals (e.g., currents) to conductive strands among strands 20 in fabric 12 to selectively adjust tension in fabric 12 and thereby selectively adjust the shape and other properties of fabric 12 (e.g., by selectively buckling fabric 12, by tightening a strap or other structure formed from fabric 12, by causing a portion of fabric 12 to protrude, and/or by otherwise adjusting fabric attributes such as tension, movement, position, shape, etc.). In some situations, tension is created in a knot in a conductive strand by passing current through that conductive strand and knot. In other situations, multiple strands are used in forming knots (e.g., from intertwined loops of material at a strand intersection location) and tension is adjusted by adjusting multiple currents through multiple respective strands.

The magnetism of a magnet embedded in a mid-strand knot can be selectively adjusted. For example, a signal can be passed through a conductive strand to magnetize an iron bar or other member formed of magnetizable material. Nodes at intersections between conductive strands can contain multiple interacting magnetic members that can be selectively magnetized. Magnetized magnetic members may also interact with magnetic fields from magnetic field sources that supply static and/or dynamic magnetic fields (globally and/or locally). The magnetic field source may include electromagnets and/or permanent magnets.

Knots can be formed at nodes where two or more conductive strands cross. Insulating strands of material can be coupled to the same nodes. For example, a conductive strand with a mid-strand knot can be used to selectively apply torque to an insulating strand that passes through the same node as the mid-strand knot (e.g., the insulating strand may pass through the mid-strand knot and may form a portion of the mid-strand knot).

Conductive strands (e.g., wires) can be knotted to provide a fabric with mid-strand knots that enable prehensile articulation of all or parts of the fabric. When a strap or other fabric-based structure is tightened (e.g., about a user's arm, wrist, head, finger, or other body part), activities such as gathering blood pressure measurements with a blood pressure sensor in sensors 26 can be facilitated). To maximize the grasping abilities of fabric 12 (e.g., the ability for fabric 12 to perform prehensile articulation), mid-strand knots can be formed at locations of fabric 12 that collectively allow fabric 12 to be constricted and expanded in response to signals from control circuitry 24. In some configurations, knots may be formed at every (or nearly every) intersection between conductive warp and weft strands. In other configurations, fabric 12 may have a sparser pattern of knots. Light-emitting diodes or other light-emitting components in optical components 14 of input-output devices 16 may be incorporated into fabric 12 (e.g., to form an array of pixels in a display or other output device). Control circuitry 24 can apply signals to the knots in patterns that encourage buckling (e.g., buckling in a region of fabric 12 that overlaps a visual output region where pixels are providing visual). For example, odd knots in each row may be provided with signals that cause the knots to increase tension, whereas even knots in that row may be provided with signals that cause the knots to decrease tension. This type of arrangement may help form fabric 12 into an accordion shape and thereby facilitate tightening of fabric 12 around a user body part of other object.

In arrangements in which multiple strands contribute to portions of a common mid-strand knot, the currents applied to the strands may, respectively, add to or subtract from the tension produced at the knot. For example, fabric in which a current-carrying strand with a knot is tied around another current-carrying strand with a knot can be used to add or subtract tension in either strand and/or associated strands (e.g., insulating strands intertwined with the current-carrying strands).

Fabric 12 may include current-carrying strands with knots woven in one or more directions within fabric 12. During operation, control circuitry 24 may be used to apply currents to the knots dynamically to dynamically control the shape (and tension, motion, etc.) of fabric 12.

The foregoing is merely illustrative and various modifications can be made to the described embodiments. The foregoing embodiments may be implemented individually or in any combination.

What is claimed is:

1. An electronic device, comprising:
input-output devices;
control circuitry configured to gather input with the input-output devices and configured to supply output with the input-output devices; and
fabric formed from strands of material, wherein the strands of material include a conductive strand of material having a mid-strand knot, wherein the control circuitry is configured to apply a signal to the conductive strand that flows through the mid-strand knot and adjusts tension in the fabric.

2. The electronic device defined in claim 1 wherein the fabric is configured to form a strap, wherein the control circuitry is configured to apply a signal to the conductive strand to tighten the strap, wherein the input-output devices include a sensor, and wherein the control circuitry is configured to gather a sensor measurement while the strap is tightened about a body part of a user.

3. The electronic device defined in claim 2 further comprising a housing, wherein the input-output devices include a display in the housing and wherein the strap is coupled to the housing.

4. The electronic device defined in claim 1 wherein the input-output devices comprise a sensor in the fabric.

5. The electronic device defined in claim 4 wherein the control circuitry is configured to receive feedback from the sensor while applying the signal to the knot to adjust the tension in the fabric.

6. The electronic device defined in claim 1 further comprising an additional conductive strand, wherein the mid-strand knot includes portions of the conductive strand and the additional conductive strand.

7. The electronic device defined in claim 1 further comprising a magnetic field source configured to apply a magnetic field to the fabric, wherein the mid-strand knot is configured to produce a magnetic field that interacts with the magnetic field applied by the magnetic field source.

8. The electronic device defined in claim 1 wherein the mid-strand knot is formed at a node in the fabric that includes a member formed from magnetic material.

9. The electronic device defined in claim 1 wherein the input-output devices comprise a sensor in the fabric, wherein the control circuitry is configured to gather feedback on the tension in the fabric from the sensor while applying the signal to the conductive strand, and wherein the sensor comprises an optical fiber sensor having an optical fiber in the fabric that is configured to measure bending in the fabric due to the tension.

10. The electronic device defined in claim 1 wherein the input-output devices comprise a sensor in the fabric, wherein the control circuitry is configured to gather feedback on the tension in the fabric from the sensor while applying the signal to the conductive strand, and wherein the sensor comprises a force sensor configured to measure the tension.

11. The electronic device defined in claim 10 wherein the input-output devices comprise a strain gauge, wherein the fabric forms a strap, and wherein the control circuitry is configured to use the strain gauge to measure tightening of the strap.

12. The electronic device defined in claim 1 wherein the input-output devices comprise a sensor in the fabric, wherein the control circuitry is configured to gather feedback on the tension in the fabric from the sensor while applying the signal to the conductive strand, and wherein the sensor comprises a force sensing resistor.

13. A system, comprising:
fabric having conductive strands of material, wherein the fabric has nodes that contain middle-of-strand knots; and
control circuitry configured to selectively adjust portions of the fabric by applying current to the middle-of-strand knots through the conductive strands of material.

14. The system defined in claim 13 wherein the conductive strands of material include first conductive strands and second conductive strands that intersect at the nodes and wherein the middle-of-strand knots are located at the nodes.

15. The system defined in claim 14 wherein the control circuitry is configured to supply first signals to the first conductive strands to produce first magnetic fields in the middle-of-strand knots and wherein the control circuitry is configured to supply second signals to the second conductive strands to produce second magnetic fields in the middle-of-strand knots.

16. The system defined in claim 15 wherein the control circuitry is configured to selectively buckle the portions of the fabric by supplying the first and second signals to cause the first and second magnetic fields to interact.

17. The system defined in claim 13 wherein each node includes magnetic material.

18. The system defined in claim 17 wherein the control circuitry is configured to magnetize the magnetic material by applying the current.

19. The system defined in claim 17 further comprising a magnetic field source configured to produce a static magnetic field to the fabric, wherein the control circuitry is configured to selectively buckle portions of the fabric by applying current to the middle-of-strand knots that causes the middle-of-strand knots to produce magnetic fields that interact with the static magnetic field.

20. Apparatus, comprising:
fabric that includes conductive strands of material, wherein the fabric includes nodes that include middle-of-strand knots each of which is formed from the conductive strands of material; and
control circuitry configured to adjust tension in the fabric by applying signals to the conductive strands that produce interacting magnetic fields in the nodes.

21. The apparatus defined in claim 20 wherein the fabric is configured to be worn on a body part.

22. The apparatus defined in claim 21 wherein the fabric is configured to form a strap that extends around the body part.

23. The apparatus defined in claim 22 further comprising a housing having a display, sensors, a battery, and wireless communications circuitry, wherein the housing is coupled to the wrist strap.

24. The apparatus defined in claim 20 wherein each node is coupled to a respective gating circuit that is configured to receive input and to adjust current flow through the middle-of-strand knot based on the input.

* * * * *